US006947134B2

(12) United States Patent
 Chang et al.

(10) Patent No.: US 6,947,134 B2
(45) Date of Patent: *Sep. 20, 2005

(54) METHOD AND INSTRUMENTATION FOR MEASURING FLUORESCENCE SPECTRA OF INDIVIDUAL AIRBORNE PARTICLES SAMPLED FROM AMBIENT AIR

(75) Inventors: Richard Chang, Hamden, CT (US); Yong-Le Pan, Cheshire, CT (US); Ronald Gene Pinnick, Columbia, MD (US); Steven Clyde Hill, Silver Spring, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 553 days.

This patent is subject to a terminal disclaimer.

(21) Appl. No.: 10/360,767

(22) Filed: Jun. 19, 2002

(65) Prior Publication Data

US 2004/0125371 A1 Jul. 1, 2004

Related U.S. Application Data

(63) Continuation-in-part of application No. 09/579,707, filed on May 25, 2000, now Pat. No. 6,532,067.
(60) Provisional application No. 60/147,794, filed on Aug. 9, 1999.

(51) Int. Cl.[7] ................................................. G01J 3/30
(52) U.S. Cl. ....................................................... 356/318
(58) Field of Search .......................................... 356/318

(56) References Cited

U.S. PATENT DOCUMENTS 5,030,002 A * 7/1991 North, Jr. ..................... 356/73
5,162,863 A * 11/1992 Ito .............................. 356/73
6,532,067 B1 * 3/2003 Chang et al. ................ 356/318

OTHER PUBLICATIONS

Ronald G. Pinnick, Steven C. Hill, Paul Nachman, and Gordon Videen, "Aerosol Fluorescence Spectrum Analyzer for Rapid Measurement of Single Micrometer–Sized Airborne Biological Particles", Aerosol Science and Technology, 28:95–104 (1998).

Ronald G. Pinnick, Steven C. Hill, Paul Nachman, and J. David Pendleton, "Fluorescence Particle Counter for Detecting Airborne Bacteria and Other Biological Particles", Aerosol Science and Technology, 23:653–664 (1995).

Paul Nachman, Gang Chen, R. G. Pinnick, Steven C. Hill, Richard K. Chang, Michael W. Mayo, and Gilbert L. Fernandez, "Conditional–Sampling Spectrograph Detection System for Fluorescence Measurements of Individual Airborne Particles"; Applied Optics, vol. 35, No. 7, Mar. 1, 1996.

Steven C. Hill, Ronald G, Pinnick, Paul Nachman Gang Chen, Richard K. Chang, Michael W. Mayo, and Gilbert L. Fernandez, "Aerosol–Fluorescence Spectrum Analyzer: Real–Time Measurement of Emission Spectra of Airborne Biological Particles"; Applied Optics, vol. 34, No. 10, Oct. 20, 1995.

(Continued)

*Primary Examiner*—Zandra V. Smith
(74) *Attorney, Agent, or Firm*—William V. Adams

(57) ABSTRACT

A Fluorescence Particle Spectrometer (FPS) performs real-time measurement of the fluorescence spectra of aerosol particles in the size range 1–10 μm diameter. The FPS has a sufficiently high sample rate (estimated to be a few liters/min) to measure aerosol within buildings (from 1 up to 600 particle fluorescence spectra per minute) at practical rates. A virtual impactor first concentrates aerosol particles, which are then drawn under negative pressure through an aerodynamic focusing nozzle in the inlet of the instrument, through the sample region, providing further concentration. The rate of particle spectra measured by the FPS increases significantly when the particle inlet is within a few meters of some common sources of indoor biological particles.

20 Claims, 10 Drawing Sheets

OTHER PUBLICATIONS

Steven C. Hill, Ronald G. Pinnick, Stanley Niles, Nicholas F. Fell, Jr., Yong–Le Pan, Jerold Bottiger, Burt V. Bronk, Stephen Holler, and Richard K. Chang, "Fluorescence From Airborne Microparticles: Dependence on Size, Concentration of Fluorphores, and Illumination Intensity", Applied Optics, vol. 40, No. 18, Jun. 20, 2001.

Steven C. Hill, Ronald G. Pinnick, Stanley Niles, Yong–Le Pan, Stephen Holler, Richard K. Chang, Jerold Bottiger, Bean T. Chen, Chung–Sing Orr, and Greg Feather, "Real–Time Measurement of Fluorescence Spectra From Single Airborne Biological Particles", Field Analytical Chemistry and Technology, vol. 3, Issues 4–5, 1999.

Yong–Le Pan, Stephen Holler, and Richard K. Chang, "Single–Shot Fluorescence Spectra of Individual Micrometer_Sized Bioaerosols Illuminated By a 351– or 266–nm Ultraviolet Laser", Optics Letters, vol. 24, No. 2, Jan. 15, 1999.

* cited by examiner

METHOD AND INSTRUMENTATION FOR MEASURING FLUORESCENCE SPECTRA OF INDIVIDUAL AIRBORNE PARTICLES SAMPLED FROM AMBIENT AIR

CROSS-REFERENCE TO RELATED APPLICATIONS

The present application is a Continuation-In-Part of U.S. patent application Ser. No. 09/579,707 filed on May 25, 2000, now U.S. Pat. No. 6,532,067 and incorporated herein by reference, which in turn claims priority from Provisional U.S. patent application No. 60/147,794 filed on Aug. 9, 1999, also incorporated herein by reference.

STATEMENT OF GOVERNMENT INTEREST

The invention described herein may be manufactured and used by or for the United States Government for governmental purposes without the payment of any royalties thereon.

FIELD OF THE INVENTION

This invention pertains generally to fluorescence spectrum analyzers and more specifically to fluorescence spectrum analyzers for measurement of bioaerosols or other single airborne particles.

BACKGROUND OF THE INVENTION

Bioaerosols, (e.g., airborne microorganisms) have both natural and anthropogenic sources. They are found in the workplace and in homes. High concentrations may occur in or around buildings with defective air handling or air-conditioning systems, in houses with domestic animals, in manufacturing operations in which metalworking fluids are used, in dairy or other operations in which animals are confined, in sites of sludge application, in recycling or composting plants, and in sewage plants. Unlike most common atmospheric aerosols, airborne microorganisms can cause diseases, and, along with other biological (e.g., dust mite allergens) and non-biological (e.g., diesel exhaust particles) aerosols can cause allergies and respiratory problems. Bioaerosols are also feared as potential biowarfare and terrorists agents.

Improved methods for measuring aerosols, particularly bioaerosols, are needed. Presently, methods that measure aerosol size distributions in real time provide almost no information about particle types and are not able to identify specific microorganisms. For most allergens, toxins, or microorganisms, culturing the sample or the use of specific protein or nucleic acid recognition molecules is required.

There are presently several methods under development which, while not able to specifically identify bioaerosol particles, can run continuously and give an indication of the presence of biological aerosols. Several fluorescence particle counter devices that measure the elastic scattering and undispersed fluorescence of single aerosol particles as they are drawn through an optical cell have been developed. These devices have demonstrated promise for differentiating between biological and at least some nonbiological aerosols. However, they hold limited promise for classifying biological aerosols. Rather primitive techniques for measuring the fluorescence spectra of single aerosol particles have also been demonstrated. However, these techniques are not capable of measuring single particle spectra with a sufficient signal-to-noise ratio to be useful for classifying micrometer-sized biological particles.

In monitoring harmful bioaerosols a rapid response may be necessary in situations where it would be impractical to continuously run a sampler/identifier (a real time monitor might also suggest when to sample for specific harmful bioaerosols). Furthermore, recognition molecules are not always available for all particle types of interest (new bioaerosols may appear). In addition, some studies of bioaerosol dynamics and reactions (evaporation, growth, agglomeration, mixing, etc.) require real-time monitoring capability. Finally, in searching for or studying intermittent sources of bioaerosols, a rapid response may be advantageous. Despite the significant advancement in capabilities of the techniques referred to above, none of these methods are capable of measuring the fluorescence spectra of single micrometer-sized biological particles with a sufficient signal-to-noise ratio to classify them.

Building a point detector that exploits the intrinsic fluorescence of bioaerosol particles for their detection and classification is technically challenging for several reasons. Particles of interest may exist as a small concentration in a dominant background. Average fluorescence spectra accumulated for a population of aerosol particles may yield little or no information about the few particles of interest (i.e., single-particle spectra are required).

In addition, fluorescence signals are weak because single particles contain only a few picograms of material, and only a small fraction of the mass of biological particles is comprised of fluorophors.

Particles are generally dispersed nonuniformly in the air (their concentration fluctuations follow the Kolmogorov spectrum of atmospheric turbulence), and they must be detected at random times as they are carried rapidly by a stream of air through an optical cell.

Moreover, an optimal detector should excite particles in the ultraviolet where most biological particles (and biological molecules) fluoresce efficiently. Ultraviolet laser sources are costly and have relatively low energy output.

Bioaerosols of interest, including individual particles in bioaerosols, may be complex mixtures. Fluorescence from various components of the mixture may limit the usefulness of classification schemes. If fluorescence emission bands were narrow and the number of possible materials in a single particle were small, then it would likely be possible to solve the inverse problem and determine the materials that contributed to the spectrum.

However, the intrinsic fluorescence bands from biological materials tend to be spectrally wide; the primary fluorophors in the majority of bioaerosols fall into only a few broad categories (e.g., the aromatic amino acids, tryptophan, tyrosine, and phenylalanine; nicotinamide adenine dinucleotide compounds (NADH); flavins; and chlorophylls); and the number of possible materials is very large. The differences between spectra of bacteria appear to depend on preparation methods (growth media, type and extent of washing of the samples, etc.) more than they depend on intrinsic variations between well-purified bacteria.

Therefore, it may not be possible, except with severely restricted classes of bioaerosols, to identify specific bioaerosols based solely on their fluorescence spectra and their size (as determined from elastic scattering). The extent to which it may be possible to characterize naturally occurring and anthropogenically produced bioaerosols (e.g., group them into a few or even a few tens of categories) is yet unknown, however, it is expected that devices according to the invention described herein will provide highly reliable and rapid bioaerosol fluorescence spectra and particle size.

Optical techniques are used extensively for aerosol measurement. They are non-intrusive, provide essentially real-time data, and are relatively easy to use. Techniques for measuring aerosol scattering using nephelometers, aerosol absorption using photo-acoustics, aerosol extinction using tranmissometry, and aerosol size and concentration using light scattering particle counters, have matured significantly over the last 25 years.

In addition to advances in hardware (for example, advances in light sources, detectors, and computers), instrument response models for some of these techniques have been developed that put the interpretation of measured data on a sound footing, thereby making the techniques more definitive for aerosol measurement.

Of the techniques mentioned above, particle counters are one of the most widely used. They have been employed for determining estimates of the tropospheric and stratospheric aerosol burden, for monitoring concentrations of particles in clean rooms, and for detecting atmospheric aerosol pollutants. However, these instruments suffer from a critical limitation they provide almost no information about particle composition.

Detecting chemical composition of particles is desirable for a variety of applications, such as in detecting fugitive aerosol pollutants, differentiating between biological and non-biological aerosols (and classifying biological particles), or investigating aerosol drug-delivery systems.

Light scattering particle counters are based on a single-particle detection approach, wherein particles entrained in air are rapidly drawn through an intense light beam, and light scattered by single particles is sensed and used to infer particle size. Recently, this approach has been expanded to measurement of the two-dimensional angular optical scattering of single aerosol particles and the intrinsic laser-induced fluorescence (LIF) of particles, both of which may be used for additional characterization. LIF can be used in addition to (or instead of) elastic scattering. These efforts concentrate on measurement of the undispersed fluorescence of particles, and consequently only have limited potential for providing information on particle composition.

More capable techniques to measure the LIF spectra of single aerosol particles have been recently developed in order to obtain better aerosol classification. In these investigations the emphasis was on detecting biological aerosols using both cw and pulsed laser sources with wavelengths ranging from 263 nm to 488 nm. As disclosed in U.S. patent application Ser. No. 09/579,707 filed on May 25, 2000, and incorporated herein by reference, a diode-pumped, solid-state, 266 nm pulsed laser source, a Schwartzchild reflective objective with large numerical aperture for collection of fluorescence, and an intensified-CCD detector mounted on the exit port of a spectrograph, may be used to measure fluorescence spectra of single bio-aerosol particles as small as 2 micrometer diameter.

However, this significant achievement is hampered by some deficiencies. The sample cell was not airtight, so the aerosol had to be forced under positive air pressure into the sample region. Thus ambient air could not be easily sampled. Further, the requirement for high laser intensity to excite fluorescence (i.e., a tightly focused UV laser beam) and small depth-of-field of the reflective objective (to allow fluorescence light to be collected over a large solid angle and focused onto the spectrograph slit) resulted in a small sample region, which was only on the order of 20 $\mu$m in diameter. The resulting sample rate (for air containing particles to be detected) was less than 0.01 liters/min, which is impractically low for most applications.

For example, this sample rate is far too low for monitoring ambient air in buildings or in work environments.

SUMMARY OF THE INVENTION

A Fluorescence Particle Spectrometer (FPS) performs for real-time measurement of the fluorescence spectra of aerosol particles in the size range 1–10 $\mu$m diameter. The FPS has a sufficiently high sample rate (estimated to be a few liters/min) to measure aerosol within buildings (from 1 up to 600 particle fluorescence spectra per minute) at practical rates. Previously reported bio-aerosol prototype detectors for measurement of single particle spectra were unable to sample the ambient environment; air containing particles had to be forced under pressure into a sample cell through a relatively small sample region. Consequently, sample rates were so small (less than 0.01 liters/min) to be impractical for most applications.

The present design overcomes these deficiencies by the use of an airtight cell that highly concentrates micrometer-sized particles. A virtual impactor first concentrates aerosol particles, which are then drawn under negative pressure through an aerodynamic focusing nozzle in the inlet of the instrument, through the sample region, providing further concentration. The rate of particle spectra measured by the FPS increases significantly when the particle inlet is within a few meters of some common sources of indoor biological particles, e.g., a person coughing, sneezing, or rubbing his skin, or the presence of a dog. The spectra obtained have a variety of spectral shapes. The FPS may be useful in a variety of areas, e.g., in studying and monitoring airborne particles that cause diseases or allergies.

Accordingly, it is an object of the present invention to provide a device that is capable of reliable and rapid fluorescence spectrum detection, particle sizing, analysis, and classification of biological aerosols. These and other objects are achieved, at least in part, by an Aerosol Fluorescence Spectrum Analyzer (AFSA) that includes an optical element which transfers light from a particle detection volume in a first focal plane to second focal plane; an aerodynamic flow system to move particles to and through the detection volume; a first trigger laser emitting a beam of wavelength $\vec{e}_1$ and focused in a trigger region through which the particles flow on their way to the detection region; a second trigger laser emitting a beam of wavelength $\vec{e}_2$ aimed in a direction approximately orthogonal to the direction of the first particle detecting beam and focused on the trigger region; a first wavelength-selective photodetector sensitive to light scattered from the trigger region and emitting an output signal in response to light of wavelength $\vec{e}_1$ in a predetermined intensity range; a second wavelength-selective photodetector sensitive to light scattered from the trigger region and emitting an output signal in response to light of wavelength $\vec{e}_2$ in a predetermined intensity range; a pulsed probe laser which emits a pulse of light centered on the particle detection volume triggered by the logically ANDed output signals of the first and second wavelength-selective photodetectors to emit a pulse of light substantially in the first focal plane but downstream from the particle detection volume; a spectral dispersing element positioned in the second focal plane; and a photosensor connected optically to the spectral dispersing element, triggered by the logically ANDed outputs of the first and second wavelength-selective photodetectors.

The apparatus set forth in the parent application has been improved in the present invention. The sample cell has been made airtight allowing for sampling of ambient air. Air containing micrometer-sized particles of interest is drawn first through an aerodynamic virtual impactor concentrator. Aerosol is then drawn from the concentrator through a conically shaped nozzle, where the aerosol particles are aerodynamically focused, providing another stage of aerosol concentration, to intersect the (fluorescence-exciting) laser beam.

This combination of virtual impactor and aerodynamic nozzle in the inlet results in the concentration of micrometer-sized particles by a factor of several thousand. In the preferred embodiment, the instrument is capable of measuring a variety of spectra in ambient laboratory air with some known sources of particles, such as coughing persons or the presence of a dog. The particulate count rate can be seen to increase when people near the instrument cough, sneeze, or rub their hands, or when a dog enters the room wagging his tail, or when the dog is petted.

The spectra recorded are quite variable. Although the spectra have not been analyzed to see what fluorescent molecules are responsible for the spectra,tryptophan is generally considered to be the contributor for the 330 nm spectral peak from biological sources. Such an instrument may be useful in a variety of applications, e.g., in monitoring the dosage of aerosolized medications, and in monitoring cat allergens, pesticides, or the spread of airborne diseases.

Various other features, objects, and advantages of the present invention and the manner in which they are achieved will become apparent after reading the following detailed description, drawings and claims.

DETAILED DESCRIPTION OF THE INVENTION

An aerosol fluorescence spectrum analyzer according to the present invention (AFSA) has distinct advantages. It may detect most bioaerosols in real time without using reagents, and be able to detect minority types of particles even when they are mixed as a tiny concentration with nonbiological particles. AFSA's according to the present invention may be useful for classifying atmospheric bio-aerosols into some as yet unknown set of classes, even for particles as small as 2 micrometers in diameter.

Aerosol Fluorescence Spectrum Analyzers (AFSAs) rapidly measure the fluorescence spectra of single micrometer-sized biological particles (and other particles) in real time. The AFSA can measure single particle spectra with good signal-to-noise making it useful for classifying biological particles Measurements that the AFSA is capable of making are technically challenging for several reasons. First, fluorescence signals are small: the AFSA detects fluorescence from single particles containing only a few picograms of material, and only a small fraction of the mass of biological particles is comprised of fluorophors. Second, since aerosol particles are mixed randomly in the air, the AFSA measures spectra of particles at random times as they are directed rapidly through an optical cell. Third, the AFSA excites fluorescence in the ultraviolet where most biological particles (and biological molecules) fluoresce efficiently.

Figure 7:
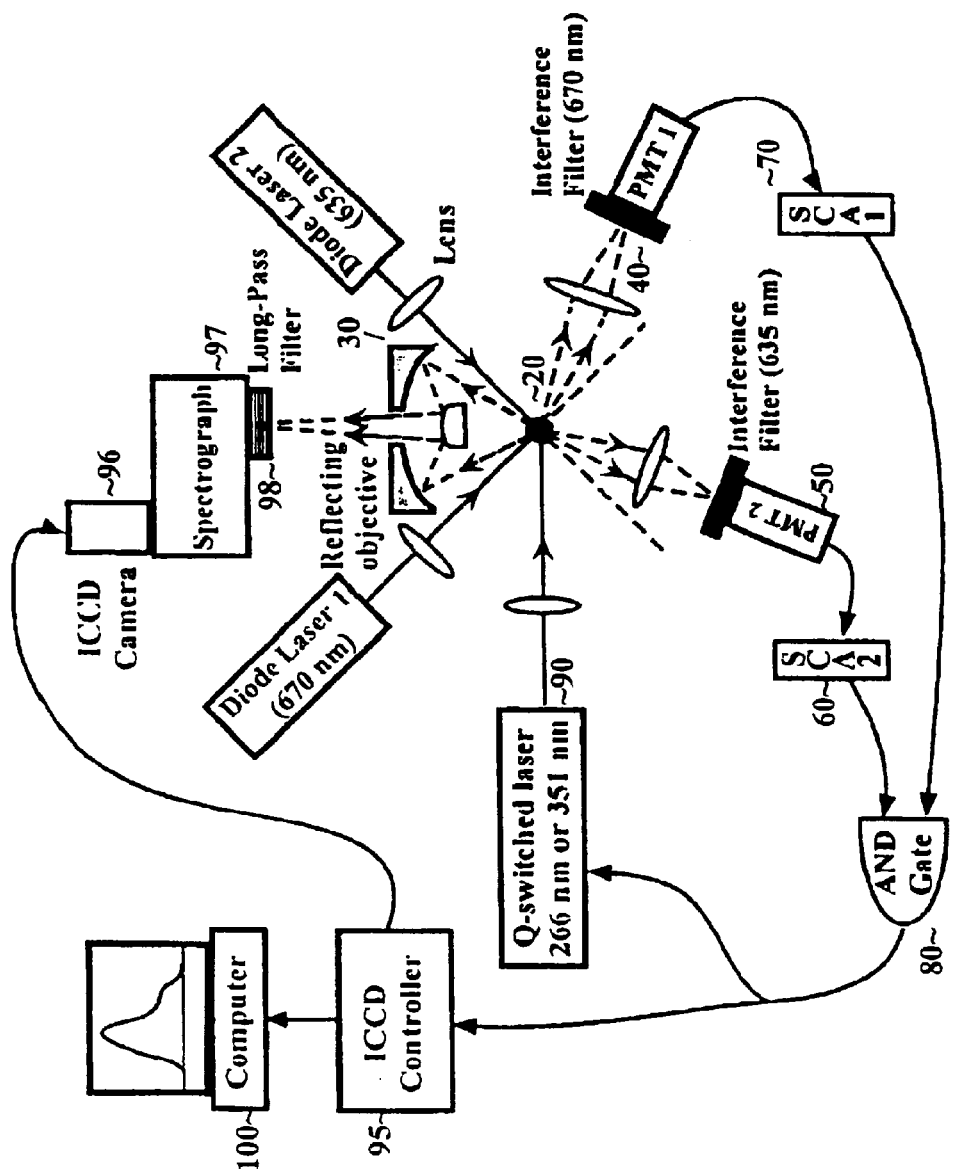
FIG. 7 is a top view schematic diagram illustrating the aerosol fluorescence spectrum analyzer according to one embodiment of the present invention.

Referring now to FIG. 7, in an ASFA constructed in accordance with one embodiment of the present invention, particles entrained within a stream of air emanating from a virtual impactor (concentrator 110 in FIG. 1), are directed downward toward a detection volume 20. As noted above, detection volume 20 is defined by two nearly orthogonal, different-wavelength diode-laser trigger beams (Diode Lasers 1 and 2, emitting light at 635 and 670 nm, respectively), which are aimed and focused precisely to define an approximate 15-$\mu$m diameter focal volume position just upstream (about 50 micron) of the first focal plane of reflecting objective 30.

As a particle from the aerodynamic flow system passes through the intersection of trigger beams from diode lasers 1 and 2 (defined as the trigger volume), light is scattered from the particle and is detected by photomultipliers (PMTs) 40 and 50. PMT 40 is equipped with a narrowband interference filter at 670 nm such that it only detects light scattered from the trigger beam from diode laser 1.

Likewise, PMT 50 is equipped with a narrowband interference filter at 635 nm so that it may only detect scattered light from the trigger beam from diode laser 2. The intensity of the scattered light may be approximately proportional to the size of the particle. To avoid detection of particles outside the size range of interest, the output signals from PMTs 40 and 50 are processed by a pair of single channel analyzers (SCA) 60 and 70 which operate as discriminators in a window mode.

The PMT output pulses must exceed a preset lower voltage level and be less than a preset higher voltage level (as set in the window mode) before the SCA may provide an output pulse. Thus, fluorescence spectra are measured only for particles falling within a preset size interval.

The two SCA outputs are fed into a logic AND gate 80, which produces an output pulse only when the SCA output signals overlap. The output of AND gate 80 triggers Q-switched UV laser 90 to fire and also turns on intensified charge coupled device (ICCD) controller 95 which activates the ICCD camera 96 to record only when Q-switched UV laser 90 fires. Thus, particles not flowing through trigger volume 20, which would not be illuminated by the central portion of the beam from Q-switched UV laser 90, and which are not in the focal region of reflecting objective 30, are ignored.

The system is completed by spectrograph 97 with long pass filter 98, which disperses the fluorescence to ICCD camera 96 and ICCD controller 95. The output of ICCD controller 95 is fed to a computer 100 where data may be displayed, stored and analyzed. In particular, pattern recognition algorithms can be employed on computer 100 to detect and classify, or at least partially characterize natural indoor and outdoor aerosols.

Various modifications and alternatives are possible. For example, in one alternative embodiment, leakage of scattering from trigger beams from diode lasers 1 and 2 may be eliminated by signaling the diode lasers to turn off using the same signal from the logic circuit as is used to trigger the pulsed UV laser 90. Probe laser 90 is preferably a tightly focused pulsed UV laser triggerable on demand and of sufficiently high intensity or fluence to excite fluorescence in microparticles.

In the preferred embodiment, Probe laser 90 was a Q-switched UV laser, either 266 nm, 4-th harmonic of a Nd:YAG laser, 30- or 70-ns pulse duration, 0.1 to 0.2 mJ per pulse (Spectra Physics models X-30 or Y-70), or 351 nm, 3rd harmonic of a Nd:YLF laser, 120 ns pulse duration, 1.65 mJ per pulse (Quantronix). The Q-switched laser was set to fire within approximately 3 microseconds of the trigger pulse (from the AND circuit), during which time the particle traveled (at a speed of about 10 m/s) about 30 micrometers. Various other probe lasers may be employed, depending on the type of particle and fluorescence to be detected.

The vertical displacement between the location where the particle is detected (trigger volume) and the location where the particle is probed (detection volume) can be compensated for by a small vertical displacement of the focal volume of trigger beams from diode lasers 1 and 2 and the beam from probe laser 90, which is focused at a focal plane of the reflecting objective.

Alternatively, the displacement of these two volumes may be compensated for by a variable electronic delay, with the delay based on the speed at which particles are introduced into the focal volume.

In another preferred embodiment, multiple-wavelength excitation (e.g., one wavelength within the absorption band for tryptophan, and a longer wavelength for other biological molecules) may be used to better identify biological particles.

Reflecting objective 30 preferably has a large numerical aperture that can collect fluorescence from the emitting particle over a large solid angle, and focus it onto the slit of a spectrograph without chromatic aberration. In a preferred embodiment, reflective objective 30 (a so-called Schwartzchild reflecting objective) is manufactured by the Ealing Company and has numerical aperture 0.5.

Alternatively, the sensitivity of the AFSA may be increased by adding a spherical reflector on the side opposite the Schwartzchild objective, or by replacing the Schwartzchild reflective objective 30 with a parabolic or ellipsoidal reflector. With this modification, particles would be excited to fluoresce when they traverse the focal point of the reflector. The parabolic reflector would collect the fluorescence, which would be focused onto the slit of spectrograph 97 as with the Schwartzchild reflecting objective. The ellipsoidal reflector may collect the fluorescence and focus it onto the slit of the spectrograph 97 positioned at the second focal point of the mirror.

In the preferred embodiment, ICCD camera 96 is manufactured by Princeton Instruments. ICCD camera 96 is placed at the exit port of the spectrograph 97 (an Acton model SP-150 with 300 grove/mm grating blazed at 500 nm, numerical aperture 0.125, input slit width 1 mm). The image intensifier of ICCD camera 96 acts as a fast shutter, opening when the targeted particle is illuminated by the UV laser. A long pass filter 98 is placed in front of spectrograph 97 to block elastically-scattered light and to pass the fluorescence.

As an alternative to the ICCD, a multiple-channel photomultiplier tube (PMT), sample-and-hold, and multiplexer can be used. The multiple-channel PMT provides the advantages of comparable sensitivity, compactness, lighter weight, and lower cost, compared to the ICCD. A 32 channel system should provide sufficient spectral resolution to classify bioaerosol particles. This refinement allows for more rapid sampling of aerosol particles, slower data rates, and more portability.

Figure 8:
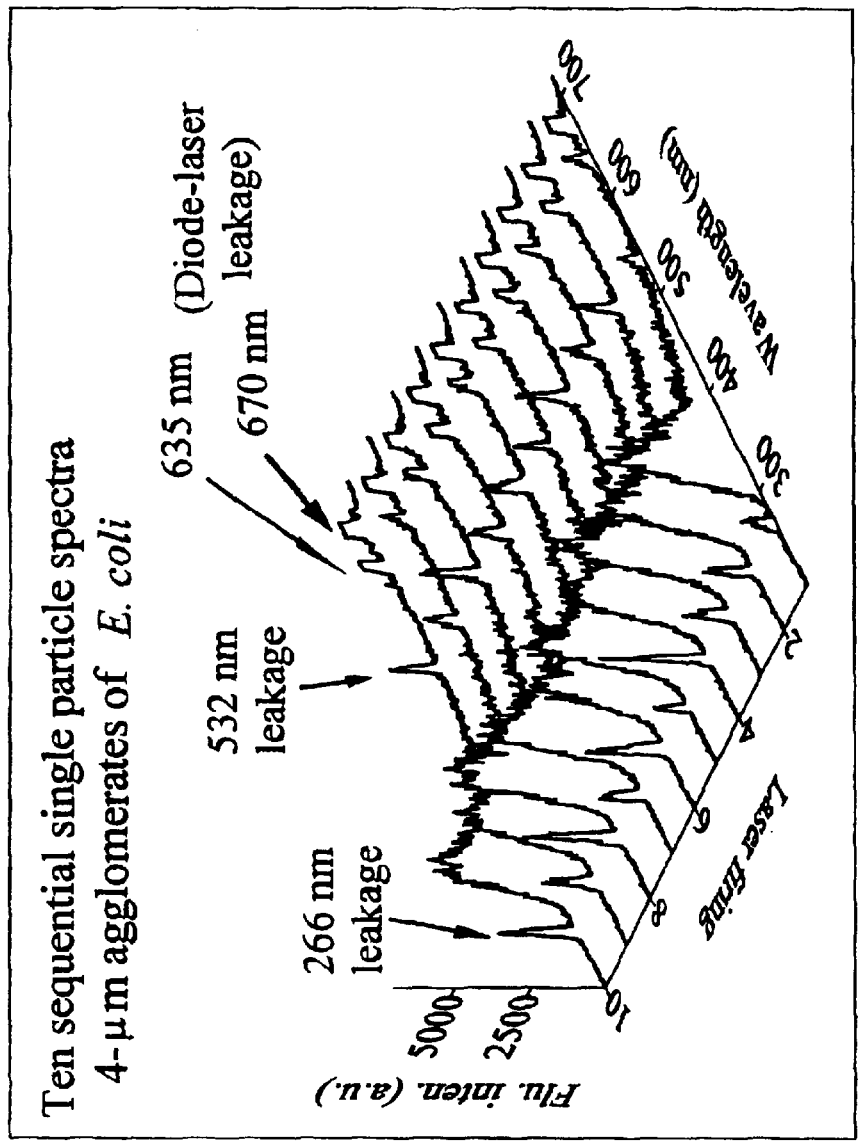
FIG. 8 is a graph illustrating ten consecutive single-particle 266-nm-excited fluorescence spectra of nominal 4 micron diameter particles composed of E. coli bacteria.
Figure 9:
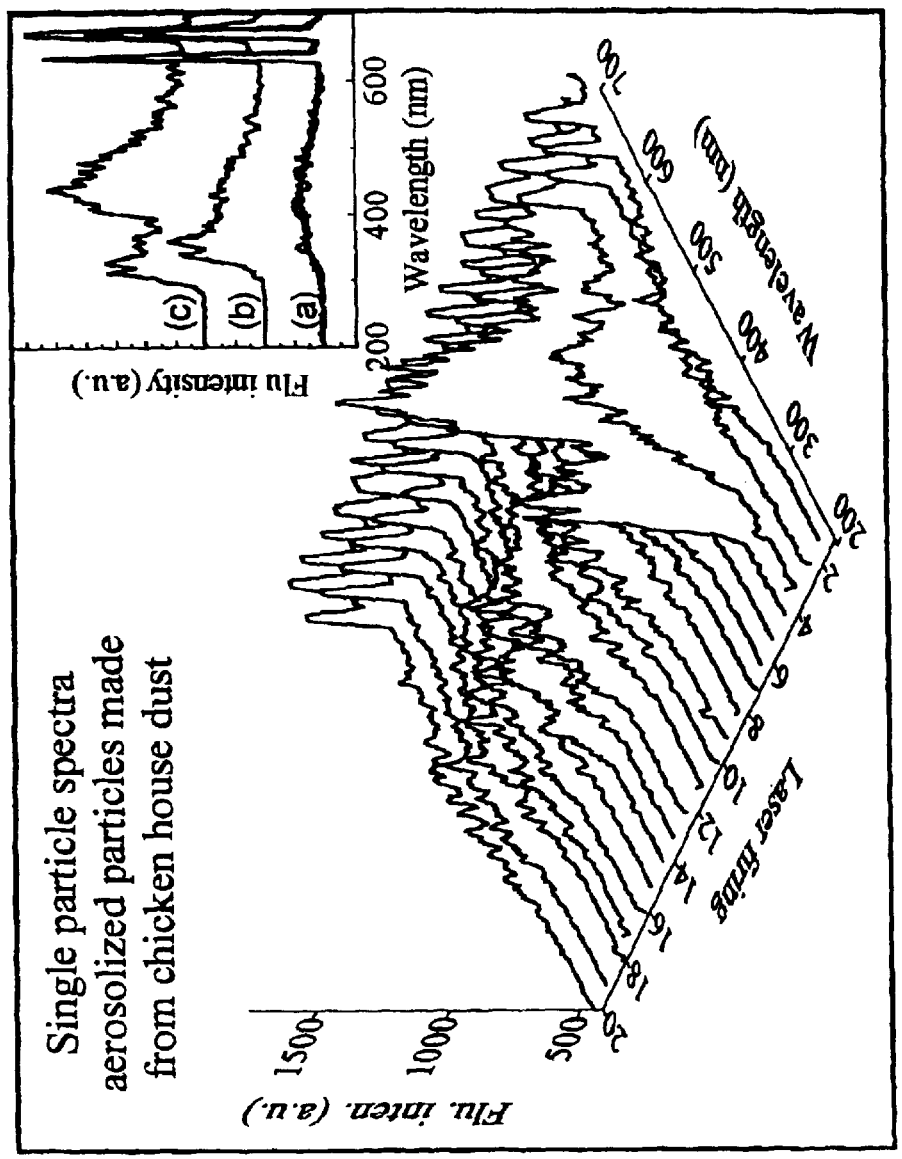
FIG. 9 is a graph illustrating twenty consecutive single-particle 266-nm-excited fluorescence spectra of aerosolized particles generated from chicken house dust of nominal average diameter of 3 microns.

The capability of the present invention is demonstrated in FIGS. 8 and 9. FIG. 8 illustrates the sensitivity and reliability of the AFSA detection system with *E. coli*. The overall fluorescence quantum efficiency of dry *E. coli* excited with 266-nm light may be about 3% of that of pure tryptophan (based on the fraction of the dry weight in tryptophan and tyrosine). The uniformity of the fluorescence spectra from single nominal 4 micron-diameter particles of dried *E. coli* is exhibited in the sequence of 10 consecutive spectra of nearly uniform particles in FIG. 8.

The broad fluorescence peak at 350 nm is mainly from tryptophan, and the tail from 400 to 500 nm is attributed to fluorescence from residues of the nutrient growth material (which may have contributions from reduced nicotinamide compounds). The sharp peaks at 266 nm, 532 nm, 635 nm, and 670 nm are from leakage of the 266-nm beam, the 532-nm beam that generates the 266-nm light, and the two cw diode lasers, respectively. (In these spectra the peaks at 266 and 532 nm are larger than in some of the subsequent figures, probably because in this figure something nearby scattered more light toward the lens—the background is sensitive to the alignment and to the position of beam blocks.) The 635-nm and 670-nm peaks have been truncated for clarity of presentation.

The spectra illustrated in FIG. 8 are similar from particle to particle and demonstrate that the system can capture, in real time, the fluorescence spectra of fairly low quantum-efficiency, micron-sized bioaerosols with a high SNR and good spectral resolution.

Unlike the uniform *E. coli* bacteria spectra illustrated in FIG. 8, the biological particles of interest for field applications may be entrained with other aerosol particles that comprise the background. Average fluorescence spectra (which are the sum of the spectra for many aerosol particles) may yield little or no information about the few particles of interest. Hence, it is important for a fieldable detector to be able to measure good-quality spectra from single particles as they are sampled from a complex mixture.

This capability of the present invention is demonstrated in FIG. 9, which illustrates 20 consecutive single-shot fluorescence spectra of particles generated from a sample collected from a chicken house. The sample was mixed with water and aerosolized using the IJAG. The average particle diameter was approximately 3 microns. Most of the fluorescence spectra are similar to the single-shot spectra labeled (a) in the inset to FIG. 9 (these have a broad emission from about 300 to 600 nm).

The more smooth line in (a) overlapping the single-shot result illustrates the average spectrum of the 100 consecutive single shots. The spectra labeled (b) and (c) in the inset show the 4th and 48th fluorescence spectra from the series of 100 single shots. These are distinctly different from the other spectra. The 4th spectrum (curve c) has a band with two peaks located near 320 nm and a broader band that peaks around 450 nm. The 48th spectrum (curve b) has its strongest emission closer to 350 nm.

Chicken house dusts are complicated, with a large variety of microbes mixed in a background of organic, inorganic, and biological matter. In the sample measured here the total culturable microbial component is only 1% of the weight, and the culturable fungal species make up less than 0.006% of the weight. The dominant bacterial species are *Staphylococcus aureus* and *Brevibacterium*.

The uniformity of the large majority of the spectra in FIG. 9 suggests that the major fluorescing component of these particles is either soluble or is in the form of very small particulates so that the fluorophors are distributed somewhat uniformly in the suspension used in the IJAG. The fact that the 4th and 48$^{th}$ spectra exhibit much larger and spectrally distinct fluorescence suggests that some of the fluorescing material is not uniformly dispersed in the suspension.

The present invention is able to differentiate these uncommon particles from the background. FIG. 9 demonstrates the capability of the AFSA to detect rare particles that are mixed with a dominant concentration of background particles.

Figure 1:
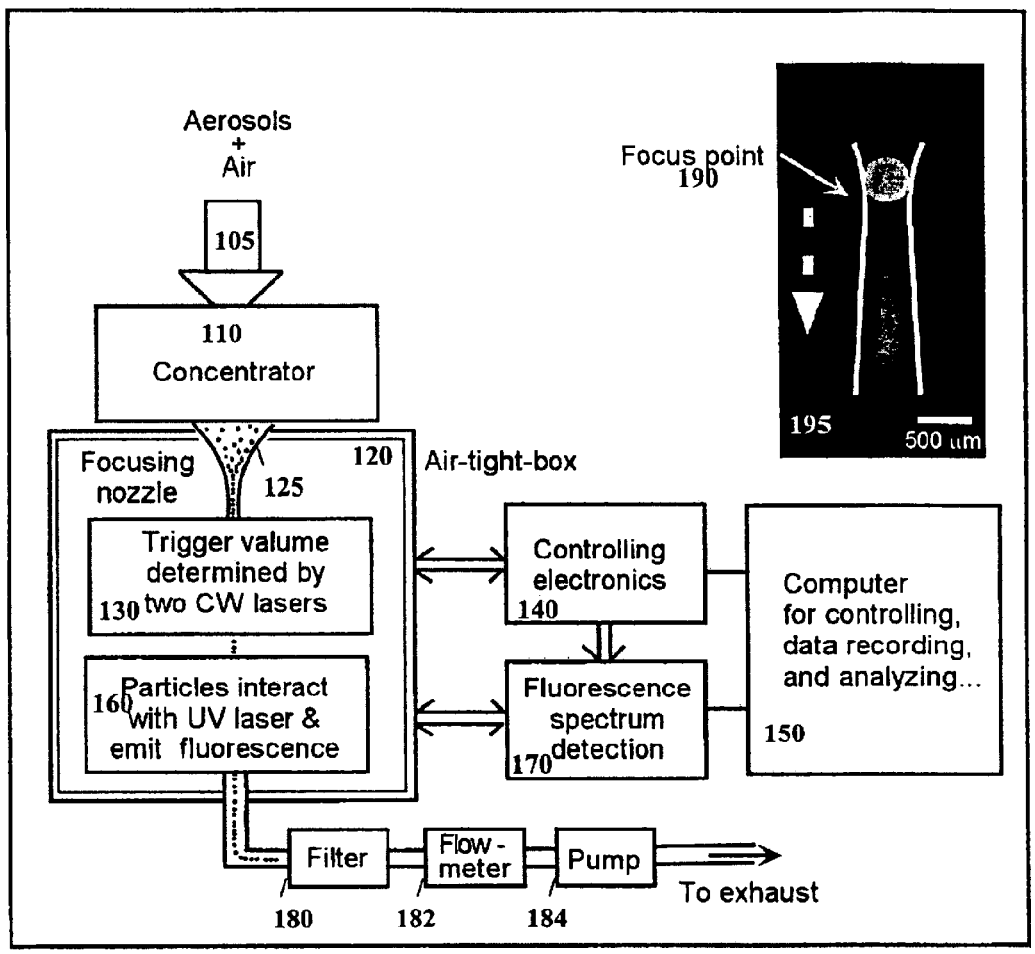
FIG. 1 is a block diagram of the Fluorescence Particle Spectrometer of the preferred embodiment of the present invention.

FIG. 1 is a block diagram of the Fluorescence Particle Spectrometer (FPS) of the preferred embodiment of the present invention. The FPS comprises of a virtual impactor/aerodynamic nozzle aerosol concentrator, trigger diode laser subsystem, UV probe pulsed laser for fluorescence excitation, reflective objective/spectrograph/ICCD detection subsystem for measurement of fluorescence, and computer.

Inset 195 (above right) is a time-exposure image of an aerosol particle jet emanating from the focusing inlet nozzle 125 having focus point 190, flowing first through the intersection of the two diode-laser beams that define the "trigger volume" 130 (this region is about 2 mm below the inlet nozzle, somewhat ellipsoidal in shape, and near the aerosol focal spot), and then (further downstream) through a sheet of light from a 532-nm laser (forming a cylindrical region). The two curved white lines have been drawn to outline the edge of the particle jet.

Ambient air containing aerosols 105 is first drawn into a virtual-impactor particle concentrator 100 (e.g., Dycor model XMX), in which particles entrained in air sampled at 500 liter/min are concentrated into a flow of about 1 liter/min. Particles in the size range 1–5 micrometer are concentrated in the exit flow with 30–40 percent efficiency. This concentrated particle-laden air may then be drawn, under negative pressure, through a conically shaped (15 degree half-angle), 1 millimeter-diameter nozzle 125, into an airtight box 120, and then through an exit port aligned with the nozzle. Nozzle 125 is described in more detail in connection with FIG. 10.

Nozzle 125 aerodynamically focuses micrometer-sized particles, providing a further concentration enhancement in a focal region about 2 millimeters below the nozzle The focal spot 190 of the particles emanating from the nozzle in this region is about 300 $\mu$m in diameter, as illustrated by the image of particles in the inset 195 of FIG. 1. This scattering image was obtained for particles crossing two diode laser beams (as described below) and a 532 nm laser beam sheet, and illustrates particle trajectories resulting in aerodynamic focusing of the aerosol jet. Focal spot 190 contains the "sample volume" described below, where a pulsed UV laser is directed to excite fluorescence in single particles as they pass through it.

The optical arrangement of this system has been described in detail above in connection with FIG. 7. Briefly, the detection system works as follows. Particles aerodynamically focused within the jet of air from nozzle 125 are directed toward a trigger volume 130 defined by the intersection of two (635- and 670-nm wavelength) focused diode laser beams. When a particle crosses both of these beams a trigger pulse is generated to fire a pulsed UV laser (266-nm Nd:YAG with 0.05 mJ energy per pulse; Spectra Physics model Y-70).

The UV laser is set to fire about 1 $\mu$s after the trigger pulse (the laser cannot fire much before 1 microsecond from the trigger), during which time the particle travels a short distance (about 20 $\mu$m) from the trigger volume to the sample volume. The sample volume is a roughly spherical region having diameter about 50 micrometer defined by the intersection of the translation of the trigger volume by 20 $\mu$m along the direction of flow, and the focal region of the collection lens.

The UV laser is focused and sufficiently intense (with fluence about 0.03 Joules/cm$^2$) to excite measurable fluorescence 160 in single particles. In addition, the laser spot size is large enough (500 $\mu$m spot size) to uniformly illuminate particles within the sample volume. The fluorescence from the particles 160 is collected by a Schwartzchild reflecting objective (Ealing) with large numerical aperture (N.A.=0.5), and focused onto a spectrograph (Acton model SP-150 with 300-groove/mm grating blazed at 500 nm; N.A 0.125) slit for dispersion.

A long-pass filter (N,N-dimethylformamide in a 1 cm cell) is placed in front of the spectrograph to block the elastic-scattered radiation (266 nm) and to pass the fluorescence. The fluorescence spectra are detected 170 by an image-intensified CCD camera (Princeton Instruments) or a 32-anode photo multiplier tube (Hamamatsu model H7260) attached to the exit port of the spectrograph.

Control electronics 140 control operation of all components with air-tight box 120 as well as generation of the trigger pulse and detection of fluorescence spectrum. Data retrieved from fluoresce spectrum detection is fed to computer 150 for data recording and analysis. Computer 150 may also be used to program control controlling electronics 140 so as to provide a central workstation for both controlling and operating the system as well as retrieving and analyzing resultant data.

Air flowing from the inlet of nozzle 125 into airtight cell 120 (an aluminum metal box which contains the trigger diode lasers and detectors, lenses, mounts, translators, and the reflecting objective) is evacuated by a pump 184 through an induction tube, which is aligned with nozzle 125 and about 2 cm below it. Pump rate can be adjustable from 0 to 3 liter/min, as measured by flowmeter 182, which determines the sample rate through the inlet of nozzle 125. The exhaust is connected to filter tube 180 (Baston) before passing through a mass flowmeter 182 (OMEGA Engineering, model 1824) and a variable speed pump 184 (KNF Neuberger, model UN05).

The overall sample rate of the FPS is dependent on particle size and determined by the flow rates into and out of the virtual impactor, particle losses in the impactor, the concentration enhancement provided by aerodynamic focusing of the inlet nozzle, and the size of the particle jet focal spot compared to the cross section of the sample volume. The virtual impactor has nominal inlet flow of 500 liters/min and delivers particles 1–5 $\mu$m in diameter with 30–40 percent efficiency for an outlet flow of 1 liter/min.

Figure 6:
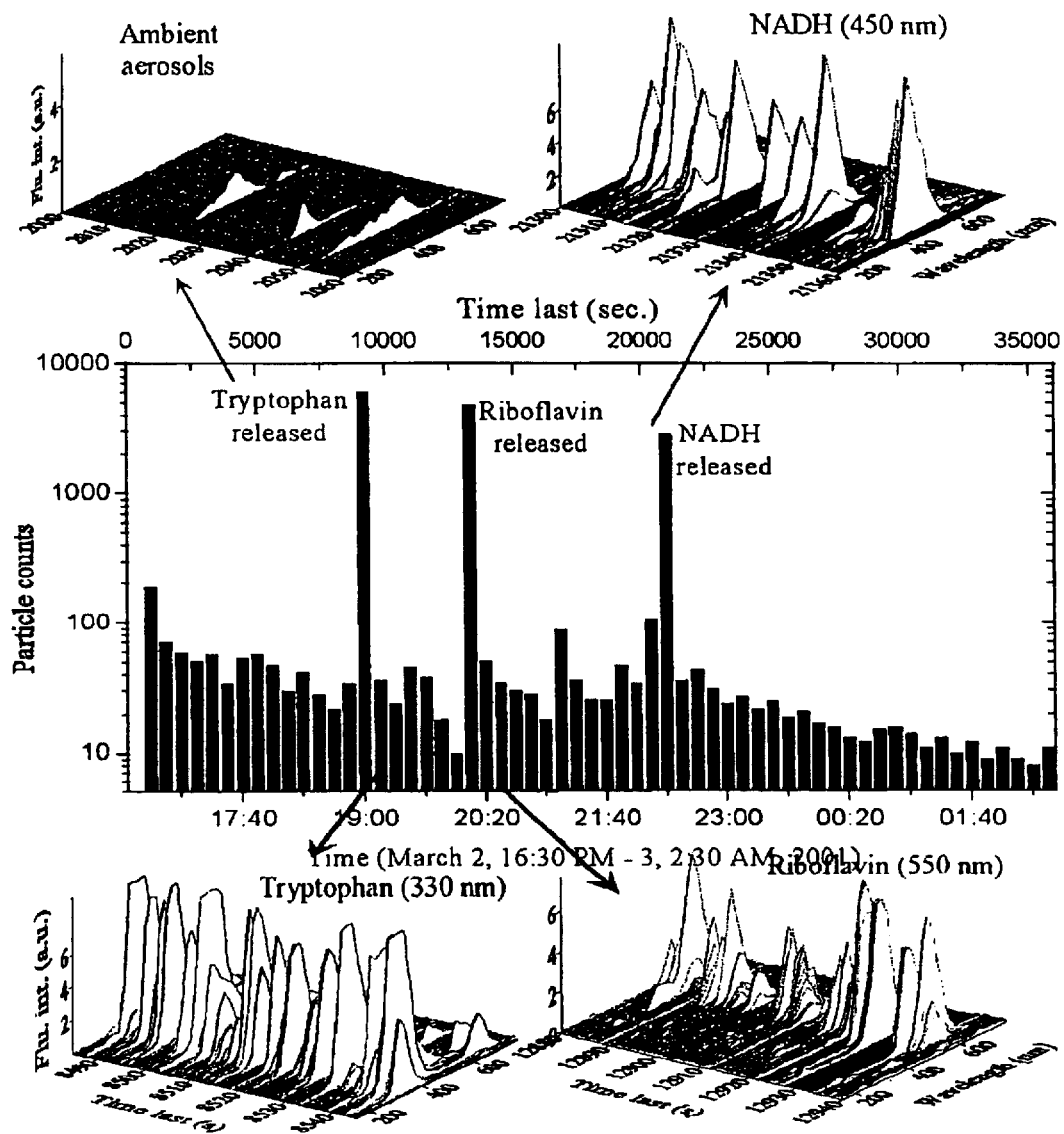
FIG. 6 is a Histogram of the number of FPS fluorescence spectra measured in 10-minute intervals.

Aerodynamic nozzle 125 focuses the particle jet to a 300-μm focal spot in the exit flow. The sample volume is estimated to be cross-sectional diameter 50 μm, which is only ⅙ that of the particle jet focal spot. Thus the overall sample rate of the FPS, for particles 1–10 μm, is estimated to be 1 to 10 liter/min. More definitive determination of FPS sample rate may require additional measurements and modeling of the aerodynamic focusing nozzle.

FIG. 2 is a graph illustrating 200 consecutive single-shot fluorescence spectra (266 nm-wavelength laser-excitation) of ambient laboratory aerosol measured with the FPS when there was no human activity for about a 20 minute period. The spectral peak near 635 nm is elastic scattering from the trigger diode laser. The inset illustrates typical spectral lineshapes in (a), (b), (c) and (d). The bottom display (e) in the inset illustrates the spectra of four of the primary fluorophors in biological aerosols for comparison.

The FPS was tested in a room with dimensions 15 m by 7 m by 5 m. The room is a research laboratory at Yale University in the basement of a large building that houses offices, classrooms, and other laboratories. FIG. 2 illustrates 200 consecutive single-shot fluorescence spectra taken over a period of about 20 minutes when no people or animals were in the room. The time was late at night, and the particle loading was as low as observed.

Line-shapes (a), (b), and (c) in the inset indicate typical spectral profiles. Nearly all of the spectral profiles reveal small fluorescence and are flat over the 400 nm to 650 nm wavelength range, as in line-shape (d) in the inset. The small sharp peaks at 266 nm and 532 nm within some of these spectra are the fourth- and second-harmonic leakages of the Nd:YAG laser. The different intensities of the sharp peaks at 635 nm, caused by the elastic scattering of one of the two diode-laser beams from the particles, is an indication of the variation of aerosol sizes measured.

Only a few of these particles fluoresce strongly. As a reference, the fluorescence spectra from four of the primary fluorophors (tyrosine, tryptophan, NADH, and riboflavin) in biological aerosols are illustrated at the bottom of the inset. Biological aerosols often have a strong peak around 330 nm resulting from tryptophan. The variation of the spectra suggests diversity in the composition of the unknown indoor aerosols.

FIG. 3 is a graph illustrating 1000 consecutive single-shot fluorescence spectra from ambient laboratory aerosols measured initially when no people were in the laboratory, and then, beginning about trace 550, while people were talking, coughing, and scratching near the FPS inlet. Typical spectral lineshapes are illustrated in the inset.

FIG. 3 illustrates the aerosol spectra measured when persons in the room were coughing, scratching, or moving within a couple meters of the concentrator inlet. The particle count rates were many times larger than when there had been no person in the room. Most of these spectra have a single peak at either 330 nm or 430 nm, similar to the spectral profiles (a) and (d) illustrated in the inset.

In some of the single-particle spectra peaks at both 330 and 430 appear with different relative intensities as in line shapes (b) and (c). The two peaks at 330 nm and 430 nm have a width of approximately 60 nm. The 330 nm peak is similar to the tryptophan peak. Nearly all the spectra have only these two peaks, but with different relative intensities. A few spectra with flat-topped peaks are caused by the saturation of the detector.

FIG. 4 is a graph illustrating 200 consecutive single-shot fluorescence spectra from ambient laboratory aerosols measured when a dog was walking and being petted near the FPS inlet. Typical spectral lineshapes are illustrated in the inset, along with the spectra from four of the primary fluorophors in biological aerosols for comparison.

The FPS spectrum capture rate greatly increased when a dog was led into the laboratory to wander and to be petted near the concentrator inlet. FIG. 4 illustrates 200 consecutive single-shot fluorescence spectra during this period. Typical spectral line-shapes are illustrated in the inset. Approximately half of the spectra have low fluorescence, similar to that in line shape (d). Line shapes (a), (b), and (c) have two peaks located at 325 nm and 430 nm with different relative intensities. These are similar to spectra illustrated in FIG. 3, except that here the peak at 430 is broader (more than 100 nm at half intensity width).

In order to investigate the response of the FPS to automobile engine emissions and their possible masking effects for detecting bio-aerosols, grab samples of both gasoline engine (a utility van) and a diesel engine (a sedan) emissions were made with 0.2 cubic meter plastic bags. The samples were obtained by connecting empty bags to the exhaust pipes of these vehicles, filling the bags, and quickly transporting them to the laboratory. The fumes in the bags were vented into the FPS virtual impactor inlet within 1 to 2 minutes of collection.

FIG. 5 is a display of 200 consecutive single-shot FPS fluorescence spectra from grab-samples of gas and diesel engine emissions. Typical spectra are illustrated for both gas (a) and diesel (b) engine emission particles. Compared to biological particles (FIGS. 2–4) the fluorescence emissions are weak. The data from FIG. 5 suggests that diesel and gasoline exhaust emissions will not mask the spectra of biological particulates.

The resulting fluorescence spectra are illustrated in FIG. 5. The fluorescence of the exhaust particles from both gasoline and diesel engines are relatively weak, especially from the diesel engine. The fluorescence from the gasoline engine illustrates two bands peaked at 320 nm and 410 nm, but with different relative intensities for different particles. The fluorescence from the diesel engine illustrates a single band centered at 400 nm. Fluorescence observation from single exhaust particles is consistent with the fluorescence spectra obtained from internal combustion engines and stationary burners.

The fluorescence spectrum from diesel and gasoline exhaust generally comprises of a UV band around 320 nm and a visible band around 400 nm, and the spectrum undergoes a red-shift with the increase in the number of aromatic rings and their molecular weight. Consequently, the fluorescence spectra may be different from the exhausts of different combustion systems with the same fuel or of the same combustion system with different fuels. Section (a) of FIG. 5 reveals that the fluorescence spectra from different exhaust particles have different relative intensities of the UV and visible band.

FIG. 6 is a Histogram of the number of FPS fluorescence spectra measured in 10-minute intervals (center). At the times indicated, powdered samples of tryptophan, riboflavin, and NADH were released near the FPS inlet for periods of about 10 seconds. Each of the four 3-dimensional displays show the consecutive spectra measured within 1 minute at the times indicated.

The FPS was run for 10 hours (from March 2, 16:30 to March 3, 2:30 am, 2001) to monitor the ambient air in the laboratory and to explore the instruments ability to measure particles at different rates by introducing contaminants. The results are illustrated in FIG. 6. During most of the 10-hour period, no one was in the laboratory. However, at the times indicated, powdered materials were released near the concentrator during periods of about 10 seconds.

The center part of FIG. 6 illustrates the histogram of the number of particles (with fluorescence spectra recorded for each particle) captured by the instrument within 10-minute intervals. The histogram reveals the expected large variations in aerosol concentration. In the first 10 minutes, the instrument measured about 200 particles, a relatively high rate, because the operator was in the room at the beginning of this period. The aerosol concentration gradually decreased until several 10's of particles were measured every 10 minutes.

The count rate rapidly increased to 6000 per 10 minutes when about 1 milligram of tryptophan powder was released near the concentrator inlet at 19:00. Then it fell to several 10's of particles per 10 minutes again. The sample rate again increased rapidly during releases of riboflavin and NADH at 20:10 and 22:20. At the times of both releases, the event rate increased to several thousand per 10-minute interval. At 21:10, two persons entered the laboratory to check on the instrument, and the sample rate increased slightly.

After 22:30, no one was in the room and few people were in the building. The laboratory ambient air became cleaner, and the number of spectra gradually decreased from several 100 to about 10 per 10 minutes. The small increase during the last 10-minute interval was due to the operator entering the laboratory to turn off the instrument, when a number of spectra were captured in the last few seconds.

Figure 2:
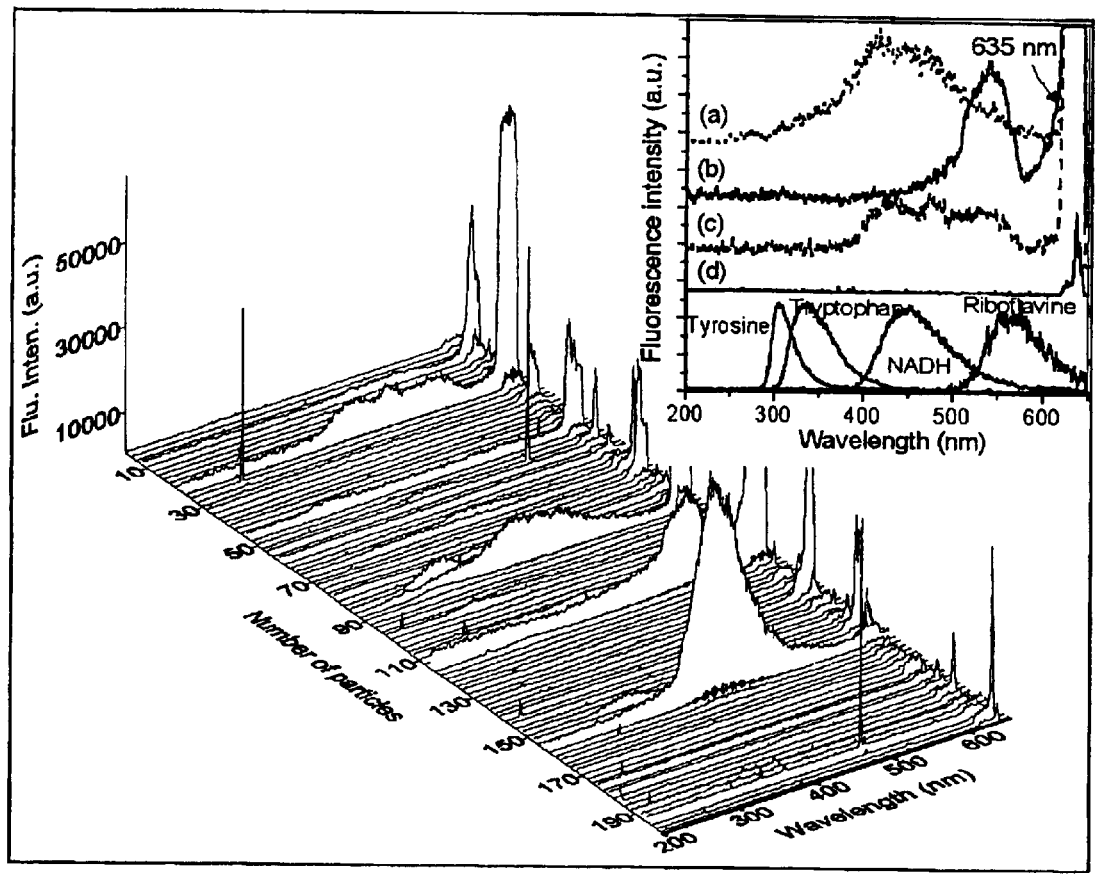
FIG. 2 is a graph illustrating 200 consecutive single-shot fluorescence spectra (266 nm-wavelength laser-excitation) of ambient laboratory aerosol measured with the FPS when there was no human activity for about a 20 minute period.
Figure 3:
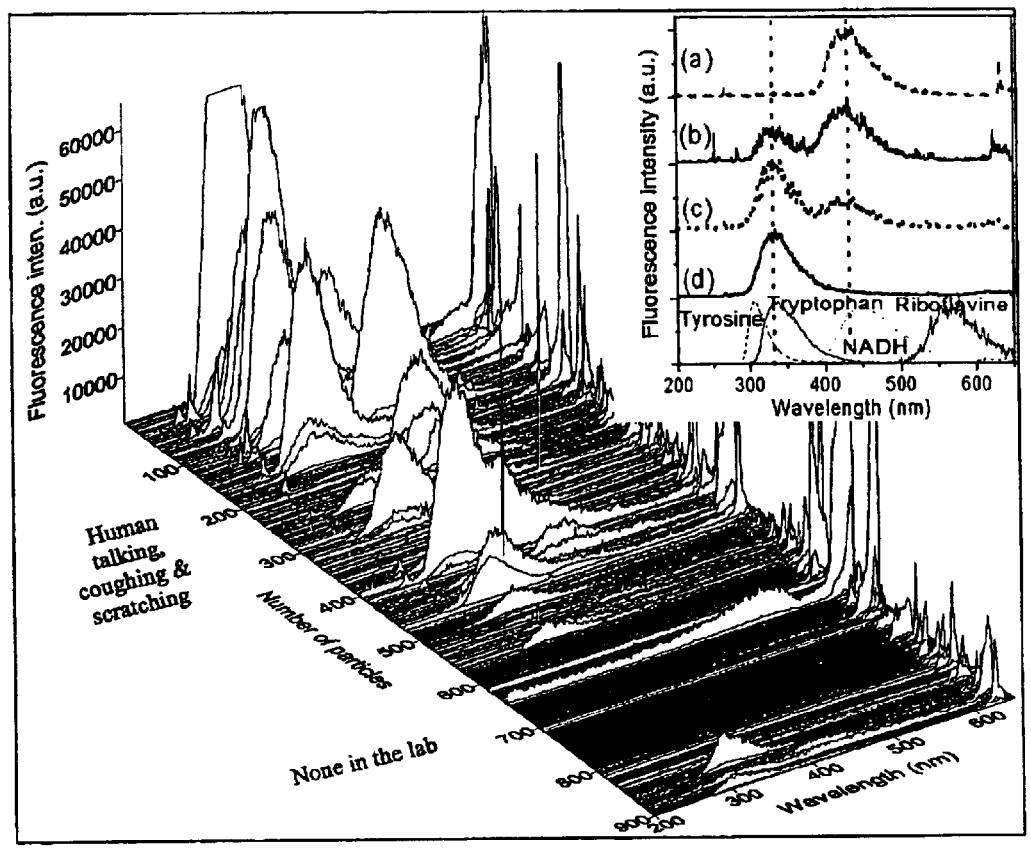
FIG. 3 is a graph illustrating 1000 consecutive single-shot fluorescence spectra from ambient laboratory aerosols measured initially when no people were in the laboratory, and then, beginning about trace 550, while people were talking, coughing, and scratching near the FPS inlet.
Figure 4:
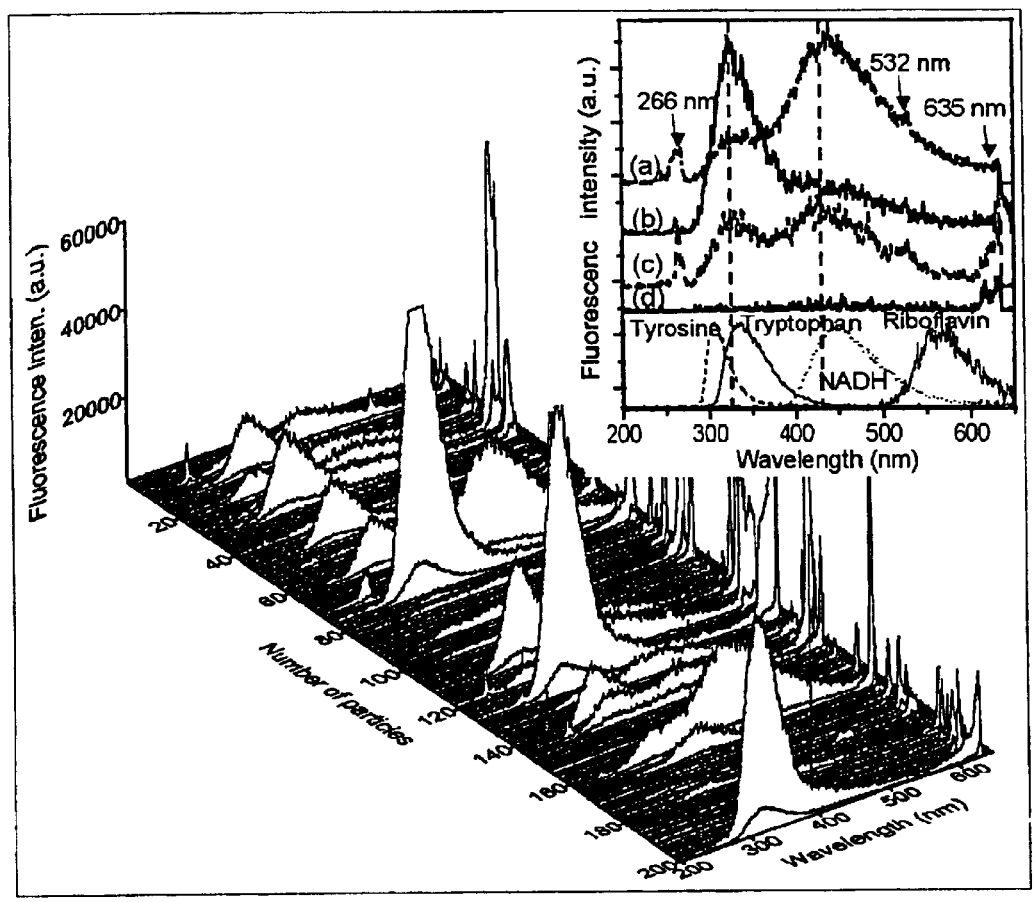
FIG. 4 is a graph illustrating 200 consecutive single-shot fluorescence spectra from ambient laboratory aerosols measured when a dog was walking and being petted near the FPS inlet.
Figure 5:
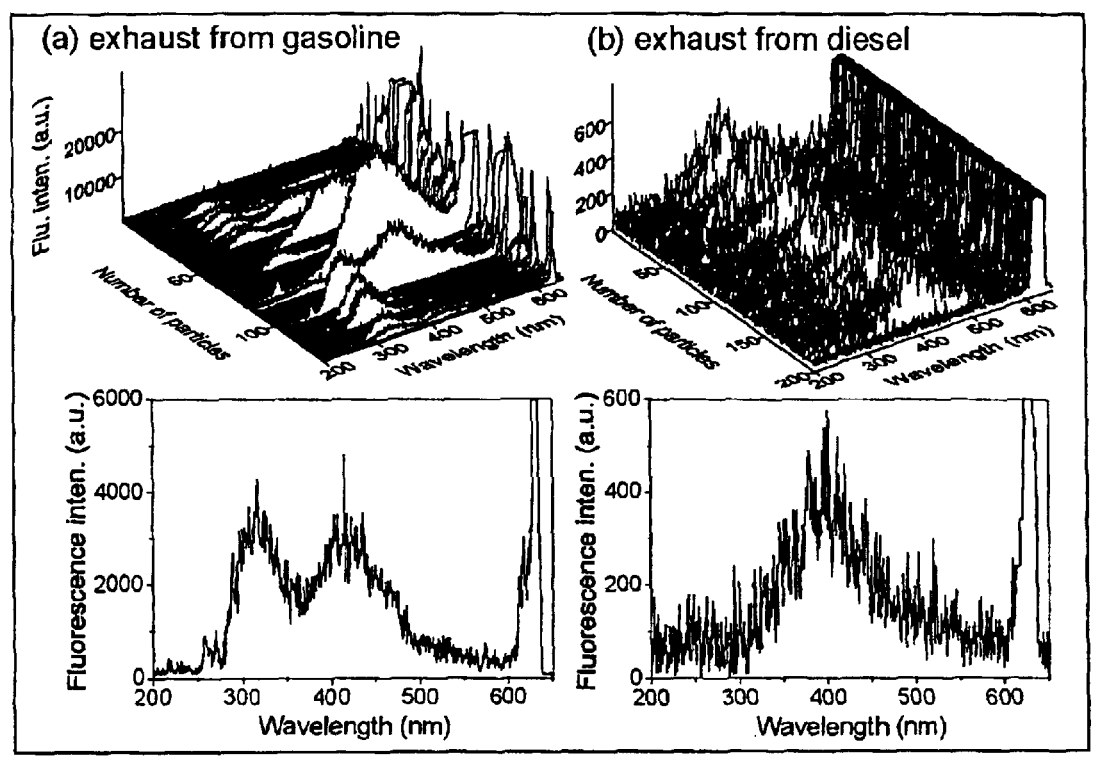
FIG. 5 is a display of 200 consecutive single-shot FPS fluorescence spectra from grab-samples of gas and diesel engine emissions.

Four 1-minute segments of this data set are also displayed in FIG. 6. In the upper left inset is a typical segment during a quiescent period (without any aerosol release). These spectra have line shapes similar to those in FIG. 2. Spectra in the upper right (NADH release), lower left (tryptophan release), and lower right (riboflavin release) are captured with much higher event rate and display the well-known fluorescence peaks at 450 nm, 330 nm, and 550 nm.

Fluorescence spectra from different aerosol sources (and from the same source) exhibit a variety of spectral shapes. The FPS may be useful in a variety of applications, e.g., in studying and monitoring airborne particles in workplace environments, and particles that cause allergies, or diseases of animals or plants.

Figure 10:
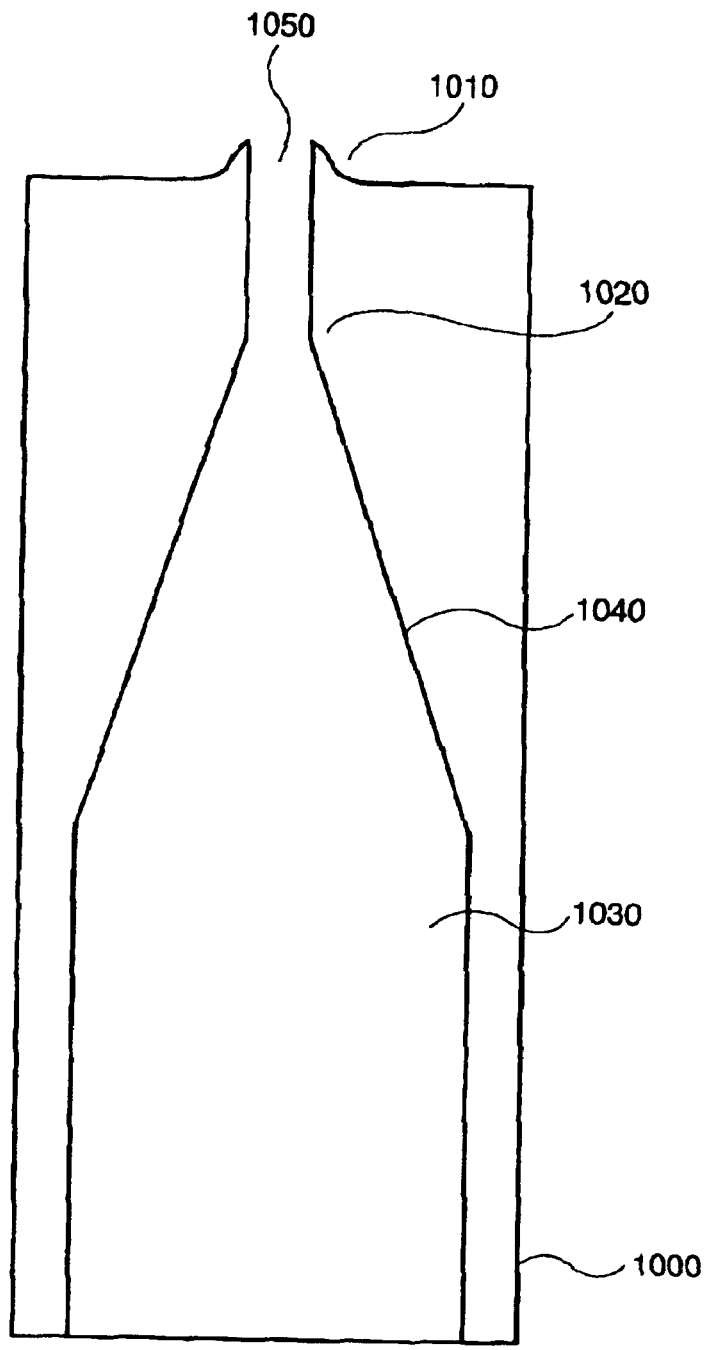
FIG. 10 is a cross-section of nozzle 125 of FIG. 1.

FIG. 10 is a cross-section of nozzle 125 of FIG. 1. The design of the nozzle, includes an approximate 18 degree angular cone 1040, a small straight section 1020 near exit port 1050, and a protruding tip 1010 at exit port 1050. The shape of nozzle 125 was achieved by a trial and error method. Computational fluid dynamics models studies are presently being done to further improve on the design.

Biological aerosols of interest, including potential biowarfare agents, could occur in small concentration (a few particles per liter of air). Nozzle 125 provides enhancement of concentration of micro-meter sized particles into a thin jet of particle laden air such that they may be probed with a tightly focused, pulsed laser beam (for exciting fluorescence) at practical sample rates. Nozzle 125 also avoids turbulent flows which would make particle trajectories chaotic.

Therefore the nozzle design requires a relatively large diameter outlet port 1050, chosen here to be about 1 mm or 0.0394 inches, allowing for a relatively large air sample rate (a few liters per minute), and aerodynamic focusing of micro-meter sized particles into an aerosol jet. The aerosol jet downstream from the nozzle has diameter significantly smaller than the nozzle outlet port diameter (perhaps 0.1 mm), providing concentration enhancements of perhaps a factor of 100 (the square of the ratio of nozzle outlet to focused aerosol jet diameters).

Further, the focused aerosol jet in this design approximately matches the diameter of the focused probe laser beam. In this way, the (relatively expensive) laser beam energy is used most efficiently, as the laser beam only illuminates a small region (with high intensity), which is about the same size as the focused aerosol jet. Laser energy is not used when no particles are present, and when the laser is pulsed to illuminate a particle, its intensity is high because it is tightly focused.

The inlet flow of the nozzle is also designed to match the outlet flow of available commercial virtual impactor concentrators (for example, the model XMX virtual impactor concentrator made by DYCOR), giving an additional stage of aerosol concentration, when used in conjunction with the nozzle. Inlet flows of commercial virtual impactor concentrators are of the order of 100 liter per minute, and they deliver 1–8 micrometer (aerodynamic diameter) particles with 40–80 percent efficiency at flows of 1 liter per minute.

While the preferred embodiment and various alternative embodiments of the invention have been disclosed and described in detail herein, it may be apparent to those skilled in the art that various changes in form and detail may be made therein without departing from the spirit and scope thereof.

We claim:

1. An Aerosol Fluorescence Spectrum Analyzer comprising:
   an optical element which transfers light from a particle detection region in a first focal plane to a second focal plane;
   an aerodynamic flow system to move particles to and through the detection region;
   a first trigger laser emitting a beam of wavelength $\ddot{e}_1$ and focused in a trigger region through which particles flow on their way to the detection region;
   a second trigger laser emitting a beam of wavelength $\ddot{e}_2$ aimed in a direction approximately orthogonal to the direction of the first trigger laser and focused on the trigger region, the trigger region being defined by the intersection of the first and second trigger laser beams;
   a first wavelength-selective photodetector sensitive to light scattered from the trigger region and emitting an output signal in response to light of wavelength $\ddot{e}_1$;
   a second wavelength-selective photodetector sensitive to light scattered from the trigger region and emitting an output signal in response to light of wavelength $\ddot{e}_2$;
   a pulsed probe laser which emits a pulse of light having a predetermined diameter, centered on the particle detection volume triggered by the logically ANDed output signals of the first and second wavelength-selective photodetectors to emit a pulse of light substantially in the first focal plane and downstream of the particle detection volume;
   a spectral dispersing element positioned in the second focal plane;
   a photosensor optically connected to the spectral dispersing element, triggered by the logically ANDed outputs of the first and second wavelength-selective photodetectors; and
   a nozzle, coupled to aerodynamic flow system, said nozzle producing a focused aerosol jet having a diameter approximately matching the predetermined diameter of the pulsed probe laser such that the pulsed probe laser illuminates a region substantially the same size as the focused aerosol jet.

2. The Aerosol Fluorescence Spectrum Analyzer of claim 1, wherein the photosensor comprises a CCD array.

3. The Aerosol Fluorescence Spectrum Analyzer of claim 1, wherein the photosensor comprises a multiple anode photomultiplier tube.

4. The Aerosol Fluorescence Spectrum Analyzer of claim 1, wherein the optical element comprises a lens.

5. The Aerosol Fluorescence Spectrum Analyzer of claim 1, wherein the optical element comprises a reflective objective.

6. The Aerosol Fluorescence Spectrum Analyzer of claim 5, wherein the reflective objective comprises a Schwartzchild optical element.

7. The Aerosol Fluorescence Spectrum Analyzer of claim 5, wherein the reflective objective comprises a parabolic optical element.

8. The Aerosol Fluorescence Spectrum Analyzer of claim 5, wherein the reflective objective comprises an ellipsoidal objective.

9. The Aerosol Fluorescence Spectrum Analyzer of claim 1, wherein the optical element comprises both a reflecting objective and a spherical reflector positioned opposite the reflecting objective.

10. The Aerosol Fluorescence Spectrum Analyzer of claim 1, wherein the pulsed laser is Q-switched.

11. The Aerosol Fluorescence Spectrum Analyzer of claim 1, wherein the pulsed laser emits light in the UV range.

12. The Aerosol Fluorescence Spectrum Analyzer of claim 1, wherein the first and second wavelength selective photodetectors comprise single channel analyzers operating in a window mode.

13. The Aerosol Fluorescence Spectrum Analyzer of claim 1, wherein the aerodynamic flow system includes means to control the direction and speed of the particle.

14. The Aerosol Fluorescence Spectrum Analyzer of claim 1, wherein at least one of the wavelength-selective photodetectors is responsive to light of a predetermined range of intensities.

15. The Aerosol Fluorescence Spectrum Analyzer of claim 1, wherein said aerodynamic flow system comprises:
   an airtight box encompassing the optical element, the first trigger laser, the second trigger laser, the first wavelength-selective photodetector, the second wavelength-selective photodetector, the pulsed probe laser, the spectral dispersing element, and the photosensor;
   a pump for evacuating air from the airtight box; and
   a flowmeter, coupled to the pump, for measuring and controlling flow of evacuated air from the airtight box,
   wherein said nozzle is mounted to an inlet of the airtight box for concentrating particles into a thin jet of focused laminar flow particle laden air such that they may be probed with the pulsed laser beam at practical sample rates.

16. An Aerosol Fluorescence Spectrum Analyzer comprising:
   triggerable pulsed laser means for fluorescence probing of a particle;
   optical means for collecting fluorescence emitted from the particle in a detection volume and for focusing it in a detection region;
   first triggering laser means for directing and focusing a beam of light of wavelength $\ddot{e}_1$ in a trigger volume substantially adjacent to the detection volume;
   second triggering laser means for directing a beam of light of wavelength $\ddot{e}_2$ in the trigger volume, in a direction approximately orthogonal to the direction of the beam emitted from the first triggering laser means;
   first sensor means for providing an output signal upon detecting light of wavelength $\ddot{e}_1$ scattered from a particle in the trigger volume;
   second sensor means for providing an output signal upon detecting light of wavelength $\ddot{e}_2$ scattered from a particle in the trigger volume;
   spectral detector means gated by ANDed outputs of the first and second sensor means for detecting fluorescence emitted from a particle and focused by the optical means in the second focal region while the triggerable pulsed laser means is in the "on" state; and
   an aerodynamic flow system including a nozzle producing a focused aerosol jet having a diameter approximately matching the predetermined diameter of the pulsed probe laser such that pulsed probe laser illuminates a region substantially the same size as the focused aerosol jet.

17. The Aerosol Fluorescence Spectrum Analyzer of claim 16, wherein at least one of the sensor means is responsive to light of a predetermined range of intensities.

18. The Aerosol Fluorescence Spectrum Analyzer of claim 16, wherein said aerodynamic flow system further comprises:
   an airtight box encompassing the optical element, the first trigger laser, the second trigger laser, the first wavelength-selective photodetector, the second wavelength-selective photodetector, the pulsed probe laser, the spectral dispersing element, and the photosensor;
   a pump for evacuating air from the airtight box; and
   a flowmeter, coupled to the pump, for measuring and controlling flow of evacuated air from the airtight box,
   wherein said nozzle is mounted to an inlet of the airtight box for concentrating particles into a thin jet of focused laminar flow particle laden air such that they may be probed with the pulsed laser beam at practical sample rates.

19. A method for fluorescence probing particles flowing in a fluid aerosol jet, comprising the steps of:
   producing, with a nozzle, a focused aerosol jet having a predetermined diameter,
   defining a trigger volume in the fluid by intersecting a plurality of substantially orthogonally aimed trigger laser beams, each of a different wavelength;
   detecting light scattered from the vicinity of the trigger volume by a plurality of particle detectors each sensitive to a wavelength corresponding to the wavelength of a trigger laser beam;
   probing the particles with a pulsed laser triggered by the particle detectors, said pulsed laser having a diameter approximately matching the predetermined diameter of fluid aerosol jet such that the pulsed laser illuminates a region substantially the same size as the focused aerosol jet;
   collecting fluorescence emitted from the particle in a detection volume and focusing it in a detection region;
   detecting the fluorescence focused in the detection region.

20. The method for fluorescence probing particles flowing in a fluid of claim 18, further comprising the step of:
   detecting light scattered from the vicinity of the trigger volume by a plurality of particle detectors each sensitive to a wavelength corresponding to the wavelength of a trigger laser beam and responsive to a predetermined range of intensities.

* * * * *